(12) United States Patent
Rosenfeld

(10) Patent No.: US 11,733,321 B2
(45) Date of Patent: Aug. 22, 2023

(54) MAGNETOMETRY BASED ON ELECTRON SPIN DEFECTS

(71) Applicant: X Development LLC, Mountain View, CA (US)

(72) Inventor: Emma Louise Rosenfeld, Palo Alto, CA (US)

(73) Assignee: X Development LLC, Mountain View, CA (US)

( * ) Notice: Subject to any disclaimer, the term of this patent is extended or adjusted under 35 U.S.C. 154(b) by 21 days.

(21) Appl. No.: 17/062,028

(22) Filed: Oct. 2, 2020

(65) Prior Publication Data

US 2021/0103010 A1    Apr. 8, 2021

Related U.S. Application Data

(60) Provisional application No. 62/909,665, filed on Oct. 2, 2019.

(51) Int. Cl.
*A61B 5/243* (2021.01)
*G01R 33/032* (2006.01)
*A61B 5/00* (2006.01)
*A61B 5/0507* (2021.01)

(52) U.S. Cl.
CPC ........ *G01R 33/0322* (2013.01); *A61B 5/0059* (2013.01); *A61B 5/0507* (2013.01); *A61B 5/243* (2021.01)

(58) Field of Classification Search
CPC .............. G01R 33/0322; A61B 5/0059; A61B 5/0507; A61B 5/243
See application file for complete search history.

(56) References Cited

U.S. PATENT DOCUMENTS

| | | | |
|---|---|---|---|
| 8,547,090 B2 | 10/2013 | Lukin et al. | |
| 8,947,080 B2 | 2/2015 | Lukin et al. | |
| 9,245,551 B2 | 1/2016 | Hallak et al. | |
| 9,541,610 B2 | 1/2017 | Kaup et al. | |
| 9,557,391 B2 | 1/2017 | Egan et al. | |
| 9,823,313 B2 | 11/2017 | Hahn et al. | |

(Continued)

FOREIGN PATENT DOCUMENTS

| | | |
|---|---|---|
| CN | 108 732 518 | 11/2018 |
| CN | 208125759 | 11/2018 |

(Continued)

OTHER PUBLICATIONS

Ajoy et al., "DC Magnetometry at the T 2 Limit," CoRR, Nov. 2016, arxiv.org/abs/1611.04691, 15 pages.

(Continued)

*Primary Examiner* — Rochelle D Turchen
(74) *Attorney, Agent, or Firm* — Fish & Richardson P.C.

(57) ABSTRACT

A magnetometer includes: a substrate; a diamond layer on the substrate, in which the diamond layer includes a defect sub-layer including multiple lattice point defects; a microwave field transmitter; an optical source configured to emit light including a first wavelength that excites the multiple lattice point defects from a ground state to an excited state; a photodetector arranged to detect photoluminescence including a second wavelength emitted from the defect sub-layer, in which the first wavelength is different from the second wavelength; and a magnet arranged adjacent to the defect sub-layer.

21 Claims, 8 Drawing Sheets

(56) References Cited

U.S. PATENT DOCUMENTS

| | | | |
|---|---|---|---|
| 9,823,314 | B2 | 11/2017 | Hahn et al. |
| 9,851,418 | B2 | 12/2017 | Wolf et al. |
| 10,006,973 | B2 | 6/2018 | Hahn et al. |
| 10,012,704 | B2 | 7/2018 | Coar |
| 10,082,545 | B2 | 9/2018 | Jeske et al. |
| 10,123,714 | B2 | 11/2018 | Hatano et al. |
| 10,126,377 | B2 | 11/2018 | Hahn et al. |
| 10,168,393 | B2 | 1/2019 | Stetson et al. |
| 10,274,551 | B2 | 4/2019 | Hruby et al. |
| 10,330,744 | B2 | 6/2019 | Luzod |
| 10,338,164 | B2 | 7/2019 | Hahn et al. |
| 10,345,396 | B2 | 7/2019 | Manickam et al. |
| 10,359,479 | B2 | 7/2019 | Manickam et al. |
| 10,379,069 | B2 | 8/2019 | Hatano et al. |
| 10,408,890 | B2 | 9/2019 | Bruce et al. |
| 10,459,041 | B2 | 10/2019 | Hahn et al. |
| 10,495,698 | B2 | 12/2019 | Jeske et al. |
| 10,502,796 | B2 | 12/2019 | Hatano et al. |
| 10,564,231 | B1 | 2/2020 | Mandeville et al. |
| 10,677,953 | B2 | 6/2020 | Stetson et al. |
| 10,712,408 | B2 | 7/2020 | Pham et al. |
| 10,753,990 | B2 | 8/2020 | Niu et al. |
| 10,816,616 | B2 | 10/2020 | Manickam et al. |
| 2014/0327439 | A1 | 11/2014 | Paola et al. |
| 2019/0018076 | A1 | 1/2019 | Hahn et al. |
| 2019/0018088 | A1 | 1/2019 | Hu et al. |
| 2019/0219645 | A1 | 7/2019 | Hahn et al. |
| 2019/0235031 | A1 | 8/2019 | Ibrahim et al. |
| 2019/0293425 | A1* | 9/2019 | Vorobyov .............. G01C 19/04 |
| 2020/0049776 | A1 | 2/2020 | Wood et al. |
| 2020/0158798 | A1 | 5/2020 | Huck et al. |
| 2020/0281499 | A1 | 9/2020 | Maeda et al. |
| 2020/0305747 | A1 | 10/2020 | Kudo et al. |
| 2020/0347515 | A1 | 11/2020 | Markham et al. |
| 2020/0348378 | A1 | 11/2020 | Alford et al. |
| 2021/0255254 | A1* | 8/2021 | Lo ......................... G01R 33/02 |

FOREIGN PATENT DOCUMENTS

| | | |
|---|---|---|
| CN | 208255383 | 12/2018 |
| CN | 106414818 | 4/2019 |
| CN | 110133545 | 8/2019 |
| CN | 110325869 | 10/2019 |
| CN | 105223521 | 2/2020 |
| CN | 210347904 | 4/2020 |
| CN | 111175678 | 5/2020 |
| CN | 111198344 | 5/2020 |
| CN | 108983121 | 7/2020 |
| CN | 111426992 | 7/2020 |
| CN | 111568418 | 8/2020 |
| CN | 110554332 | 1/2021 |
| DE | 102018202588 | 8/2019 |
| DE | 102018208055 | 11/2019 |
| DE | 102018214617 | 3/2020 |
| DE | 102018216033 | 3/2020 |
| DE | 102018220234 | 5/2020 |
| DE | 102019203929 | 9/2020 |
| DE | 102019203930 | 9/2020 |
| EP | 3242139 | 11/2017 |
| EP | 3373023 | 9/2018 |
| GB | 2574643 | 12/2019 |
| JP | 2009236599 | 10/2009 |
| JP | 2011095106 | 5/2011 |
| JP | 2012159427 | 8/2012 |
| RU | 2607840 | 1/2017 |
| WO | WO2019168097 | 9/2019 |
| WO | WO2020157497 | 8/2020 |

OTHER PUBLICATIONS

Barry et al., "Sensitivity Optimization for NV-Diamond Magnetometry," CoRR, Mar. 2019, arxiv.org/abs/1903.08176, 73 pages.

Bougas et al., "On the Possibility of Miniature Diamond-Based Magnetometers Using Waveguide Geometries," Micromachines, Jun. 2018, 9(6):276.

Chipaux et al., "Magnetic imaging with an ensemble of nitrogen-vacancy centers in diamond," European Physical Journal D: Atoms, Molecules, Clusters Andoptical Physics, EDP Sciences. Jul. 2015, 69(7):1-10.

Jensen et al., "Cavity-enhanced room-temperature magnetometry using absorption by nitrogen-vacancy centers in diamond," Phys. Rev. Lett., Apr. 2014, 112:160802.

Jensen et al., "Magnetometry with Nitrogen-Vacancy Centers in Diamond: In: High Sensitivity Magnetometers," Smart Sensors Measurement and Instrumentation, 2017, 15 pages.

Kim et al., "CMOS-Integrated Diamond Nitrogen-Vacancy Quantum Sensor," CoRR, Oct. 2018, arxiv.org/abs/1810.01056, 7 pages.

PCT Invitation to Pay Additional Fees in International Appln. No. PCT/US2020053781, dated Jan. 19, 2021, 16 pages.

Toraille et al., "Optical Magnetometry of Single Biocompatible Micromagnets for Quantitative Magnetogenetic and Magnetomechanical Assays," Nano Letters, Dec. 2018, 18(12):7635-7641.

Yeung et al., "Anti-reflection coating for nitrogen-vacancy optical measurements in diamond," Applied Physics Letters, Jun. 2012, 100(25):251111.

Alday et al., "Comparison of Electric- and Magnetic-Cardiograms Produced by Myocardial Ischemia in Models of the Human Ventricle and Torso," Plos One, 2016, 11(8):e0160999.

Backus et al., "A prospective validation of the HEART score for chest pain patients at the emergency department," International Journal of Cardiology, 2013, 168:2153-2158.

Barry et al., "Optical magnetic detection of single-neuron action potentials using quantum defects in diamond," PNAS, Dec. 2016, 113(49):14133-14138.

Bartington.com [online] "MAG-13," 2020, retrieved on Oct. 5, 2020, retrieved from URL <https://www.bartington.com/mag-13/>, 4 pages.

Bison et al., "A room temperature 19-channel magnetic field mapping device for cardiac signals," Applied Physics Letters, 2009, 95(17):173701.

Cubells-Beltrán et al., "Integration of GMR Sensors with Different Technologies," Sensors (Basel), Jun. 2016, 16(6):939.

Cyclotronroad.org [online] "Connecting Minds and Machines," May 28, 2018, retrieved on Oct. 2, 2020, retrieved from URL <https://www.cyclotronroad.org/sonera>, 5 pages.

Dale et al., "Medical applications of diamond magnetometry: commercial viability," CoRR, May 2017, https://arxiv.org/pdf/1705.01994.pdf, 10 pages.

Dale et al., "The Construction of a Graphene Hall Effect Magnetometer," IEEE Sensors Journal, 2018, 18(23):9534-9541.

Deans et al., "Sub-picotesla widely tunable atomic magnetometer operating at room-temperature in unshielded environments," CoRR, Aug. 2018, arxiv.org/abs/1804.05124, 10 pages.

Elhosni et al., "Magnetic field SAW sensors based on magnetostrictive-piezoelectric layered structures: FEM modeling and experimental validation," Sensors and Actuators A: Physical, 2016, 240:41-49.

Faley et al., "Superconducting Quantum Interferometers for Nondestructive Evaluation." Sensors, Dec. 2017, 17(12):2798.

Fenici et al., "Thirty years of clinical magnetocardiography at the Catholic University of Rome: Diagnostic value and new perspectives for the treatment of cardiac arrhythmias," International Journal of Cardiology, Oct. 2013, 168(5):5113-5115.

Gemsys.ca [online] "Near-Continous Surveys Improve Definition of Magnetic Anomalies," 2016, retrieved on Oct. 5, 2020, retrieved from URL <http://www.gemsys.ca/wpcontent/uploads/2016/05/Capture5.jpg?lbisphpreq=1>, 1 page.

Grinolds et al., "Nanoscale magnetic imaging of a single electron spin under ambient conditions," CoRR, Sep. 2012, arXiv:1209.0203v1, 12 pages.

Hailer et al., "The Value of Magnetocardiography in Patients with and Without Relevant Stenoses of the Coronary Arteries Using an Unshielded System," Pacing and Clinical Electrophysiology, 2005, 28(1):8-16.

Hall et al., "Monitoring ion-channel function in real time through quantum decoherence," PNAS, Nov. 2010, 107(44):18777-18782.

(56) References Cited

OTHER PUBLICATIONS

Herrera-May et al., "Recent Advances of MEMS Resonators for Lorentz Force Based Magnetic Field Sensors: Design, Applications and Challenges," Sensors, Sep. 2016, 16(9):1359.

Hrvoic et al., "Brief Review of Quantum Magnetometers," GEM Advanced Magnetometers, Sep. 2012, 15 pages.

Karaveli et al., "Modulation of nitrogen vacancy charge state and fluorescence in nanodiamonds using electrochemical potential," PNAS, Apr. 2016, 113(15):3938-3943.

Karo et al., "Magnetocardiogram measured by fundamental mode orthogonal fluxgate array," Journal of Applied Physics, 2015, 117(17):17B322.

Korhonen et al., "Increased Intra-QRS Fragmentation in Magnetocardiography as a Predictor of Arrhythmic Events and Mortality in Patients with Cardiac Dysfunction After Myocardial Infarction," Journal of Cardiovascular Electrophysiology, Nov. 2005, 17(4):396-401.

Kumar et al., "Amplitude modulated Lorentz force MEMS magnetometer with picotesla sensitivity," Journal of Micromechanics and Microengineering, Sep. 2016, 26(10):105021.

Kwong et al., "Diagnostic value of magnetocardiography in coronary artery disease and cardiac arrhythmias: A review of clinical data," International Journal of Cardiology, 2013, 167(5):1835-1842.

Lim et al., "Usefulness of Magnetocardiogram to Detect Unstable Angina Pectoris and Non-ST Elevation Myocardial Infarction," The American Journal of Cardiology, Feb. 2009, 103(4):448-454.

Mooney et al., "A portable diagnostic device for cardiac magnetic field mapping," Biomed. Phys. Eng. Express, 2017, 3(015008): 10 pages.

Pannetier-Lecoeur et al., "GMR-based sensors for ultra-sensitive magnetometry," IEEE Sensors 2009 Conference, pp. 1856-1859.

Pannetier-Lecoeur et al., "Magnetocardiography with GMR-based sensors," J. Phys.Conf. Ser., 2011, 303(012054): 6 pages.

Pappas, "High Sensitivity Magnetic Field Sensor Technology Overview," National Institute of Standards & Technology, Jun. 2010, 50 pages.

Park et al., "Magnetocardiography Predicts Coronary Artery Disease in Patients with Acute Chest Pain," Annals of Noninvasive Electrocardiology, Jul. 2005, 10(3):312-323.

Pnicorp.com [online] "RM3100 Geomagnetic Sensor," May 25, 2018, retrieved on Oct. 2, 2020, retrieved from URL <https://www.pnicorp.com/rm3100/>, 7 pages.

Quspin.com [online] "QTFM," Jul. 13, 2017, retrieved on Oct. 2, 2020, retrieved from URL <https://quspin.com/qtfm/>, 2 pages.

Quspin.com [online] "QTFM: UAV MAD Survey," Sep. 14, 2018, retrieved on Oct. 2, 2020, retrieved from URL <https://quspin.com/qtfm-uav-mad-survey/>, 1 page.

Rybalko et al., "New type of fluxgate magnetometer for the heart's magnetic fields detection," Current Directions in Biomedical Engineering, Sep. 2015, 1(1):22-25.

Schirhagl et al., "Nitrogen-Vacancy Centers in Diamond: Nanoscale Sensors for Physics and Biology," Annual Review of Physical Chemistry, Apr. 2014, 65:83-105.

Schloss et al., "Simultaneous Broadband Vector Magnetometry Using Solid-State Spins," CoRR, Mar. 2018, arXiv:1803.03718v2, 13 pages.

Senggottuvel et al., "Feasibility study on measurement of magnetocardiography (MCG) using fluxgate magnetometer," AIP Conference Proceedings, 2018, 1942(0600180): 5 pages.

Shah et al., "A Compact, High Performance Atomic Magnetometer for Biomedical Applications," Phys. Med. Biol,. Nov. 2013, 58(22):8153-8161.

Shin et al., "Incremental diagnostic value of combined quantitative and qualitative parameters of magnetocardiography to detect coronary artery disease," International Journal of Cardiology, Nov. 2016, 228:948-952.

Smith et al., "Comparison of magnetocardiography and electrocardiography: a study of automatic measurement of dispersion of ventricular repolarization," EP Europace, Oct. 2006, 8(10):887-893.

Tolstrup et al., "Non-Invasive Resting Magnetocardiographic Imaging for the Rapid Detection of Ischemia in Subjects Presenting with Chest Pain," Cardiology, 2006, 106(4):270-276.

Twinleaf.com [online] "VMR Magnetoresistive Vector Magnetometer," Dec. 10, 2019, retrieved on Oct. 2, 2020, retrieved from URL <https://twinleaf.com/vector/VMR/>, 3 pages.

Wikipedia.org [online] "Orders of magnitude (magnetic field)," last edited Sep. 4, 2020, retrieved on Oct. 5, 2020, retrieved from URL <https://en.wikipedia.org/wiki/Orders_of_magnitude_(magnetic_field)>, 3 pages.

Wood et al., "T2-limited sensing of static magnetic elds via fast rotation of quantum spins," CoRR, Dec. 2018, arXiv:1802.03845v2, 9 pages.

Zhang et al., "Magnetic Sensing of Magnetization in Magnetotactic Bacteria with Nitrogen Vacancy Centers in Dimond," 2017 5th International Conference on Enterprise Systems, Nov. 2017, 4 pages.

International Preliminary Report on Patentability in International Appln. No. PCT/US2020/053781, dated Apr. 14, 2022, 14 pages.

PCT International Search Report and Written Opinion in International Appln. No. PCT/US2020053781, dated Mar. 12, 2021, 24 pages.

Ahmadi et al., "Pump-Enhanced Continuous-\Vave 1\fagnetometry Using Nitrogen-Vacancy Ensembles," Phys. Rev Applied, 2017, 8:034001.

Office Action in European Appln. No. 20796973.4, dated Mar. 23, 2023, 5 pages.

Office Action in Japanese Appln. No. 2022-518918, dated Apr. 20, 2023, 8 pages (with English translation).

\* cited by examiner

MAGNETOMETRY BASED ON ELECTRON SPIN DEFECTS

CROSS-REFERENCE TO RELATED APPLICATION

This application claims the benefit of the filing date of U.S. Provisional Application No. 62/909,665, filed on Oct. 2, 2019. The contents of U.S. Application No. 62/909,665 are incorporated herein by reference in their entirety.

BACKGROUND

Various sensors are available that rely on classical physical phenomena for detecting properties such as electric or magnetic fields. In certain cases, magnetic field detectors are limited by one or more of their sensitivity, dynamic range and/or form factor.

SUMMARY

The present disclosure relates to electron spin defect based magnetometry. The details of one or more embodiments are set forth in the accompanying drawings and the description below. Other features, objects, and advantages of the invention will be apparent from the description and drawings, and from the claims.

In general, in some aspects, the subject matter of the present disclosure encompasses a magnetometer that includes: a substrate; an electron spin defect layer on the substrate, wherein the electron spin defect layer comprises a plurality of lattice point defects; a microwave field transmitter; an optical source configured to emit light comprising a first wavelength that excites the plurality of lattice point defects from a ground state to an excited state; an optical resonator cavity comprising at least a portion of the electron spin defect layer and arranged to recycle the light through the electron spin defect layer; a photodetector arranged to detect photoluminescence comprising a second wavelength emitted from the electron spin defect layer, wherein the first wavelength is different from the second wavelength; and a magnet arranged adjacent to the electron spin defect layer.

Implementations of the magnetometer may include one or more of the following features. For example, in some implementations, the substrate comprises silicon or silicon carbide. The substrate may include a microwave field control circuit coupled to the microwave field transmitter to provide the microwave field transmitter with a microwave source signal, in which the microwave field control circuit is optionally configured to output the microwave source signal as a pulsed microwave source signal, in which the microwave field control circuit is optionally configured to output the microwave source signal at a frequency between about 50 MHz and about 4 GHz.

In some implementations, the substrate comprises an optical source control circuit coupled to the optical source to provide the optical source with an optical control signal.

In some implementations, the substrate comprises a microprocessor, wherein the microprocessor is coupled to the photodetector to receive a light measurement signal from the photodetector and wherein the microprocessor is configured to analyze the light measurement signal to determine characteristics of a time-dependent magnetic field to which the magnetometer is exposed.

In some implementations, the plurality of lattice-point defects comprises a plurality of nitrogen-vacancy (NV) defects, wherein the electron spin defect layer comprises a diamond layer comprising carbon 12 and/or carbon 13.

In some implementations, the plurality of lattice-point defects comprises a plurality of silicon-carbide (SiC) defects.

In some implementations, the electron spin defect layer has a thickness of between about 1 micron and about 1 mm.

In some implementations, the electron spin defect layer comprises a thickness of between about 200 microns and about 5 millimeters.

In some implementations, the microwave field transmitter comprises an antenna.

In some implementations, the microwave field transmitter comprises a patterned layer of metal on a surface of the electron spin defect layer or at an interface of the electron spin defect layer and another layer of material.

In some implementations, the microwave field transmitter comprises a co-planar waveguide, loop, wire, or coil.

In some implementations, the optical source comprises a light emitting diode or a laser.

In some implementations, the wavelength of light from the optical source is about 532 nm.

In some implementations, the optical source is arranged to emit the light in a direction towards the electron spin defect layer. The optical source may be arranged to emit the light towards the electron spin defect layer such that the light travels through the electron spin defect layer and impinges on an interface of the electron spin defect layer at an angle greater than a total internal reflection critical angle of the interface.

In some implementations, the magnetometer include at least one optical component arranged between the optical source and the electron spin defect layer, wherein the at least one optical component is positioned to direct the light from the optical source through the electron spin defect layer and towards an interface of the electron spin defect layer at an angle greater than a total internal reflection critical angle of the interface.

In some implementations, the at least one optical component comprises a lens, a mirror, a diffraction grating, and/or a beam-splitter.

In some implementations, the optical resonator cavity comprises a plurality of mirrors. At least one mirror of the plurality of mirrors may be partially transmissive to the wavelength of light from the optical source and is arranged between the optical source and the electron spin defect layer. At least one mirror of the plurality of mirrors may include a stack of dielectric layers having alternating refractive index.

In some implementations, the substrate comprises a recess, wherein the electron spin defect layer is seated within the recess, wherein the recess comprises at least one reflective sidewall facing the electron spin defect layer to reflect the light from the optical source towards the electron spin defect layer or to redirect the light from the optical source that has been reflected from the electron spin defect layer.

In some implementations, the photodetector is positioned directly on the electron spin defect layer. The photodetector may be positioned so that a detecting surface of the photodetector faces an area of the electron spin defect layer from which the light from the optical source is reflected or refracted. The microwave field transmitter may be positioned adjacent to the area of the electron spin defect layer to which the light from the optical source is directed.

In some implementations, the magnetometer includes at least one lens between the electron spin defect layer and the photodetector.

In some implementations, the magnetometer includes at least one optical filter between the electron spin defect layer and the photodetector. The at least one optical filter may be configured to filter out wavelengths of light different than the second wavelength.

In some implementations, the magnet is a permanent magnet.

In some implementations, the electron spin defect layer is secured to the substrate through an adhesive.

In some implementations, the magnetometer includes an enclosure, wherein the substrate, the electron spin defect layer, the microwave field transmitter, the optical source, the optical resonator cavity, the photodetector and the magnet are contained in the enclosure.

In some implementations, the enclosure is configured to attach to an article of clothing.

In some implementations, the enclosure is configured to removably adhere to human skin.

In some implementations, the substrate, the electron spin defect layer, the microwave field transmitter, the optical source, the optical resonator cavity, the photodetector and the magnet are arranged on a single chip.

In some implementations, the magnetometer includes a rotating platform, wherein the single chip is secured to the rotating platform having an axis of rotation, and the rotating platform is configured to spin the single chip around the axis of rotation.

In some implementations, the magnetometer includes a rotating platform, wherein the single chip is secured to the rotating platform having an axis of rotation, and the rotating platform is configured to oscillate the single chip around the axis of rotation.

In some implementations, a sensitivity of the magnetometer without rotation is less than 100 pT/√Hz, and wherein a sensitivity of the magnetometer during rotation is between about 50 pT/√Hz and 1 pT/√Hz or below.

In general, in some other aspects, the subject matter of the present application relates to methods of performing magnetocardiography using a magnetometer, in which the magnetometer comprises an electron spin defect layer comprising a plurality of lattice point defects, a microwave field transmitter, an optical source, a photodetector and a magnet, the method including: rotating the magnetometer around a rotation axis and relative to a first time-varying magnetic field of a first frequency so that the magnetometer experiences a second time-varying magnetic field of a second frequency that is greater than the first frequency, wherein the first time-varying magnetic field is emitted from a heart; directing, during the rotation of the magnetometer, light from the optical source toward the electron spin defect layer, wherein the light comprises a first wavelength that excites the plurality of lattice point defects from a ground state to an excited state; detecting, during the rotation of the magnetometer, a photoluminescence from the electron spin defect layer using the photodetector to provide a measurement signal, wherein the photoluminescence comprises a second wavelength that is different from the first wavelength; and determining, from the measurement signal, information about the first time-varying magnetic field.

In some implementations, rotating the magnetometer comprises continuously spinning the magnetometer around the rotation axis.

In some implementations, rotating the magnetometer comprises oscillating the magnetometer around the rotation axis at a rotation angle of less than 360 degrees.

In some implementations, directing the light from the optical source toward the electron spin defect layer comprises directing the light from the optical source through the electron spin defect layer so that the light impinges on an interface of the electron spin defect layer at an angle greater than a total internal reflection critical angle of the interface. Directing the light from the optical source toward the electron spin defect layer may include redirecting, using an optical resonator cavity, totally internally reflected light from the interface of the electron spin defect layer back to the interface of the electron spin defect layer.

In some implementations, the method includes applying a microwave signal to the electron spin defect layer, wherein applying the microwave signal optionally comprises applying a series of microwave pulses, wherein the series of microwave pulses is optionally a dynamical decoupling pulse sequence. The series of pulses may include a first pi/2 pulse, one or more pi pulses subsequent to the first pi/2 pulse, and a second pi/2 pulse subsequent to the first pi pulse. The one or more pi pulses may be applied at a same time as a zero-crossing of the second time-varying magnetic field. A frequency of rotation of the magnetometer may be greater than a frequency of the first time-varying magnetic field. The frequency of the first time-varying magnetic field may be less than 400 Hz.

In some implementations, the magnetometer comprises a microwave field control circuit, the method further comprising applying a microwave source signal from the microwave field control circuit to the microwave field transmitter so that the microwave field transmitter emits a microwave field toward the electron spin defect layer, wherein the microwave source signal is optionally a pulsed microwave source signal, wherein a microwave frequency of the microwave source signal is optionally between about 50 MHz and about 4 Ghz.

In some implementations, the magnetometer comprises a microwave field control circuit to generate the microwave source signal.

In some implementations, the method includes prior to rotating the magnetometer, sweeping a frequency of the microwave source signal over a predetermined range; and identifying a reduction in photoluminescence from the photodetector at a first microwave frequency within the predetermined range to locate an electron spin resonance frequency.

In some implementations, the magnetometer comprises an optical source control circuit, the method further comprising providing an optical control signal from the optical source circuit to the optical source to generate the light comprising the first wavelength.

In some implementations, the first wavelength is about 532 nm.

In some implementations, determining information about the first time-varying magnetic field comprises: extracting a quantum phase accumulation from the measurement signal; and determining a vector of the first time-varying field, the magnitude of the first time-varying magnetic field, a phase of the first time-varying magnetic field or both the magnitude and the phase of first time-varying magnetic field from the quantum phase accumulation.

In some implementations, the method includes attaching an enclosure comprising the magnetometer to an article of clothing.

In some implementations, the method comprises adhering an enclosure comprising the magnetometer to skin.

DETAILED DESCRIPTION

The present disclosure relates to electron spin defect based magnetometry. In particular, the present disclosure relates to techniques for sensing magnetic fields by monitoring Zeeman shift of electron spin sublevels established by the presence of atomic defects in solid-state lattice structures, and devices for performing the same.

More specifically, electron spin defect based magnetometers include quantum sensors that leverage the occurrence of an electronic spin defect in a solid state lattice, where the spin can be both initialized and read out optically. In certain implementations, the defect may arise as an atomic-level vacancy in a lattice structure, such as a vacancy occurring near a nitrogen atom substituted in place of a carbon atom within diamond. Accordingly, a single spin defect center, as an atom-scale defect, may be used to detect magnetic fields with nanometer spatial resolution, while an ensemble of uncorrelated spin defects may be used with spatial resolution given by the ensemble size (e.g., on the order of microns) typically with an improvement in sensitivity given by $\sqrt{N}$, where N is the number of spin defects. Moreover, in some implementations, electron spin defect based magnetometers may exhibit relatively long coherence times, such as times approaching 1 second or more. Additionally, electron spin defect based magnetometers may be operated at room temperature and, in certain cases, within relatively compact structures, allow for portability and reduction in magnetometer costs, which may be advantageous in health related applications such as measuring magnetic fields emanating from the heart.

Figure 1:
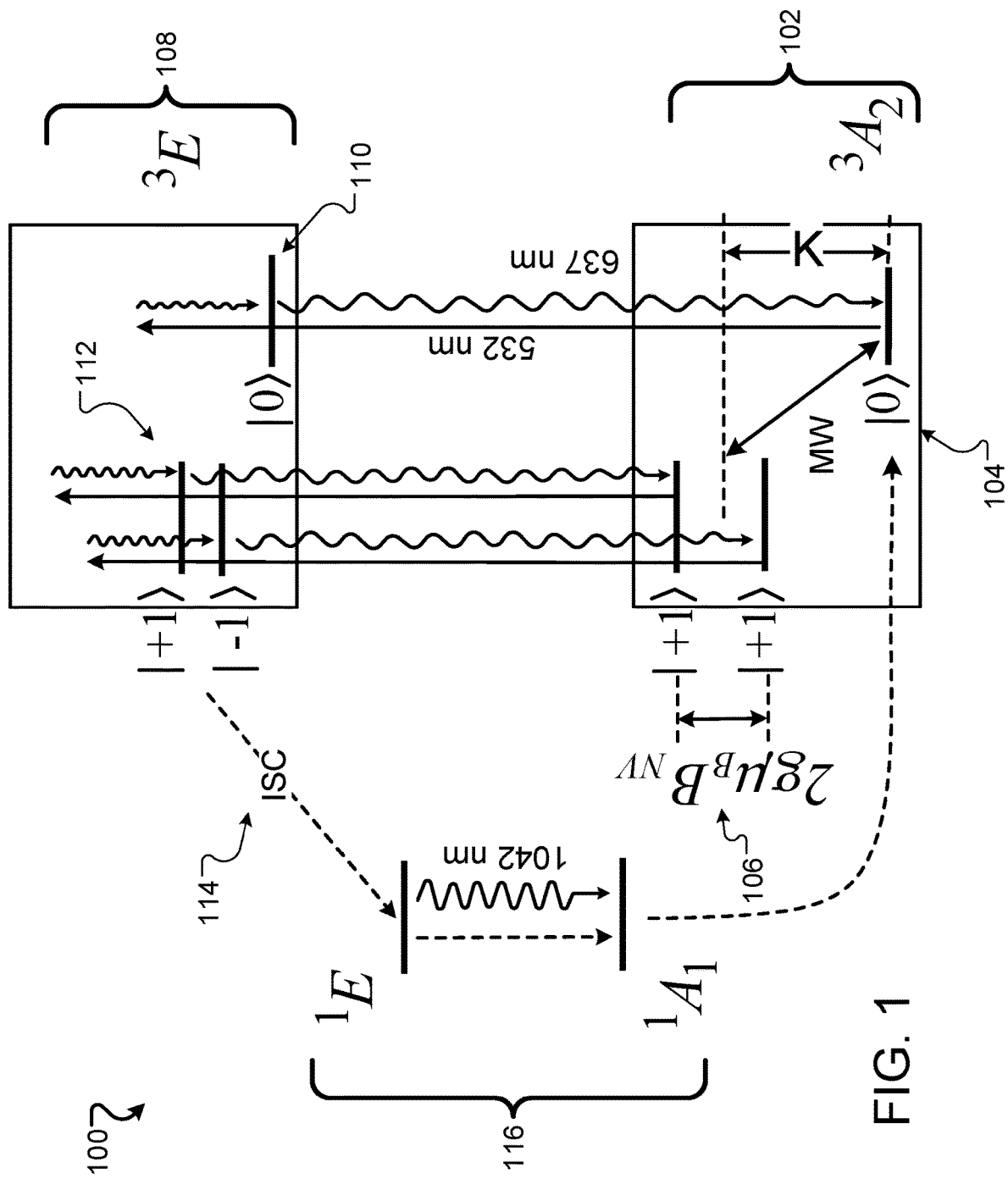
FIG. 1 is a schematic that illustrates an exemplary energy level scheme for a nitrogen-vacancy defect.
Figure 2:
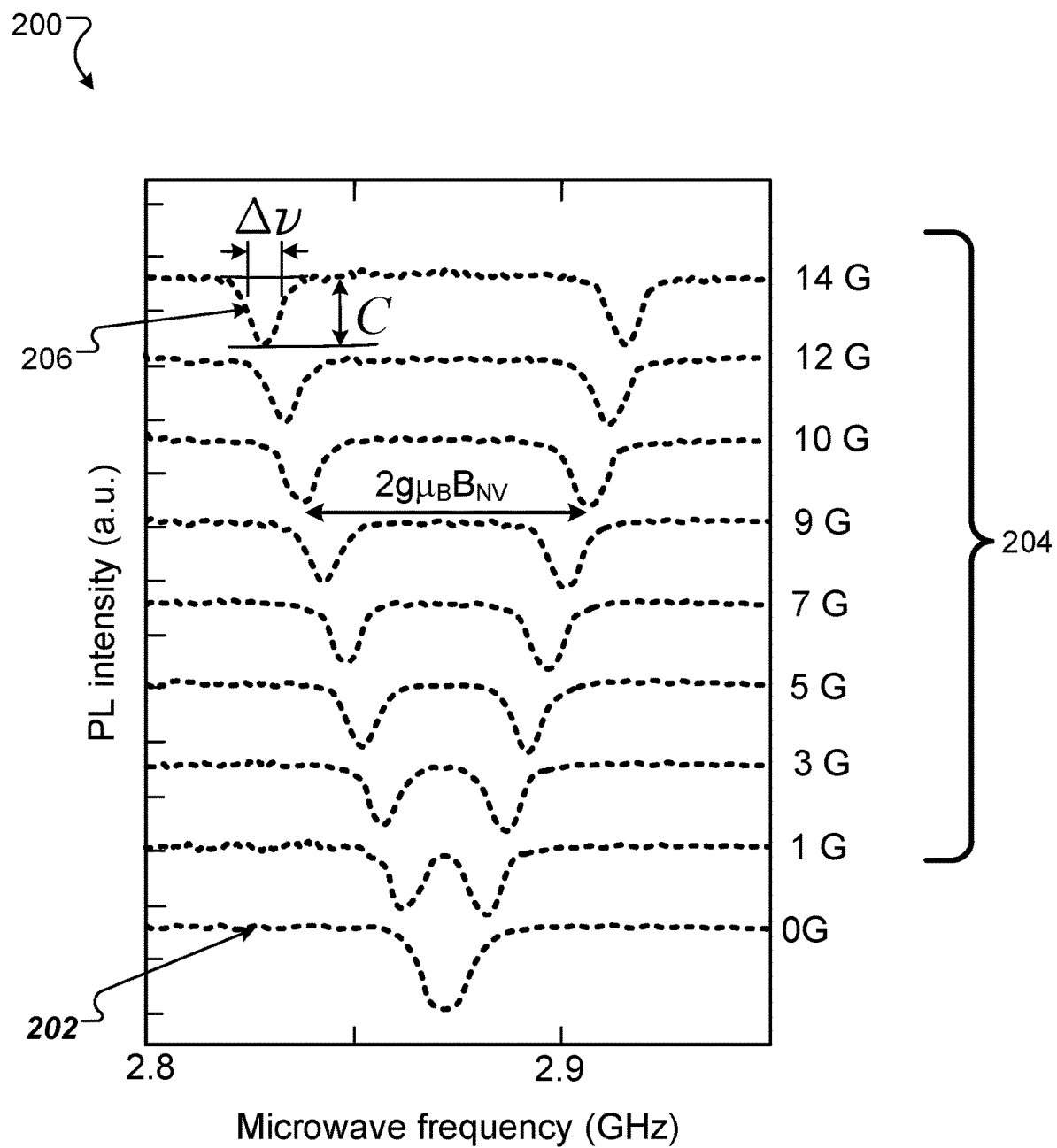
FIG. 2 is a plot of exemplary photoluminescence intensity versus applied microwave frequency.

A brief description of electron spin defect based magnetometry will be described with reference to FIGS. 1-2 and in particular with respect to nitrogen vacancy (NV) magnetometry, though the techniques and devices disclosed herein may be applicable to other materials, including other types of electron spin defects, as well. An NV center is a defect in a diamond lattice that contains a substitutional nitrogen atom in place of carbon, adjacent to a vacancy in the diamond lattice. The negatively-charged state of the defect provides a spin triplet ground level which can be initialized, coherently manipulated with long coherence time and readout, using optical means. FIG. 1 is a schematic that illustrates an energy level scheme 100 for an NV defect. The NV defect behaves as an artificial atom within the diamond lattice that exhibits a broadband photoluminescence emission with a zero phonon line at 1.945 eV or $\lambda_{PL}=637$ nm. Moreover, the ground level 102 of the NV defect is a spin triplet state, having spin sub-levels of the $m_s=0$ state 104 and the $m_s=+/-1$ states 106, separated by K=2.87 GHz in the absence of a magnetic field. The defect can be optically excited to an excited level 108, which also is a spin triplet having an $m_s=0$ state 110 and $m_s=+/-1$ states 112. Once optically excited into the excited level 108, the NV defect can relax primarily through one of two mechanisms: a) through a radiative transition and phonon relaxation, thus producing a broadband red photoluminescence; or b) through a secondary path 114 that involves non-radiative intersystem crossing to singlet states 116.

The decay path branching ratios from the excited state manifold back to the ground state manifold depends on its initial spin sublevel projection. Specifically, if the electron spin began in the $m_s=+/-1$ states, there is approximately a 30% chance for the spin to decay non-radiatively through the secondary path 114, down to the $m_s=0$ state. The population of the spin sublevels can be manipulated by the application of a resonant microwave field to the diamond. Specifically, at a particular microwave frequency corresponding to the transition energy cost between the 0 and +/-1 states, transitions occur between those sublevels, resulting in a change in the level of photoluminescence of the system. In particular, if the spin is initialized into the ms=0 state, and the population is transferred to one of the +/-1 states by the resonant microwave drive, the photoluminescence rate upon subsequent optical illumination will decrease. In the absence of a magnetic field, this drop in photoluminescence may be observed by sweeping the microwave frequency, as depicted in the bottom-most photoluminescence (PL) intensity line 202 shown in FIG. 2, which is a plot of PL intensity versus applied microwave frequency. Upon applying a magnetic field in the vicinity of the NV defect, however, the degeneracy of the $m_s=+/-1$ spin sublevels is lifted by the Zeeman effect, leading to the appearance of two electron spin resonance (ESR) transitions, corresponding to dips in the PL spectrum (see upper PL lines 204 in FIG. 2). The value Av corresponds to the ESR linewidth, typically on the order of 1 MHz and the value C is the ESR contrast. To detect small magnetic fields, the NV transitions may be driven at the point of maximum slope (see, e.g., 206 in FIG. 2). At this point of maximum slope, a time-domain change in the photoluminescence may be detected, from which a time-domain change in magnetic field can be derived. The signal may be expressed as $(\delta I_0/\delta B) \times \delta B \times \Delta t$, where $I_0$ is the NV defect PL rate, $\delta B$ is the infinitesimal magnetic field variation, and $\Delta t$ is the measurement duration, much smaller than the timescale on which the magnetic field changes A single NV defect therefore can serve as a magnetic field sensor with an atomic-sized detection volume. To improve sensitivity, a collective response of an ensemble of NV defects may be detected, such that the collected PL signal is magnified by the number N of the sensing spins and therefore improves the shot-noise limited magnetic field sensitivity by a factor of $1/\sqrt{N}$.

Figure 3:
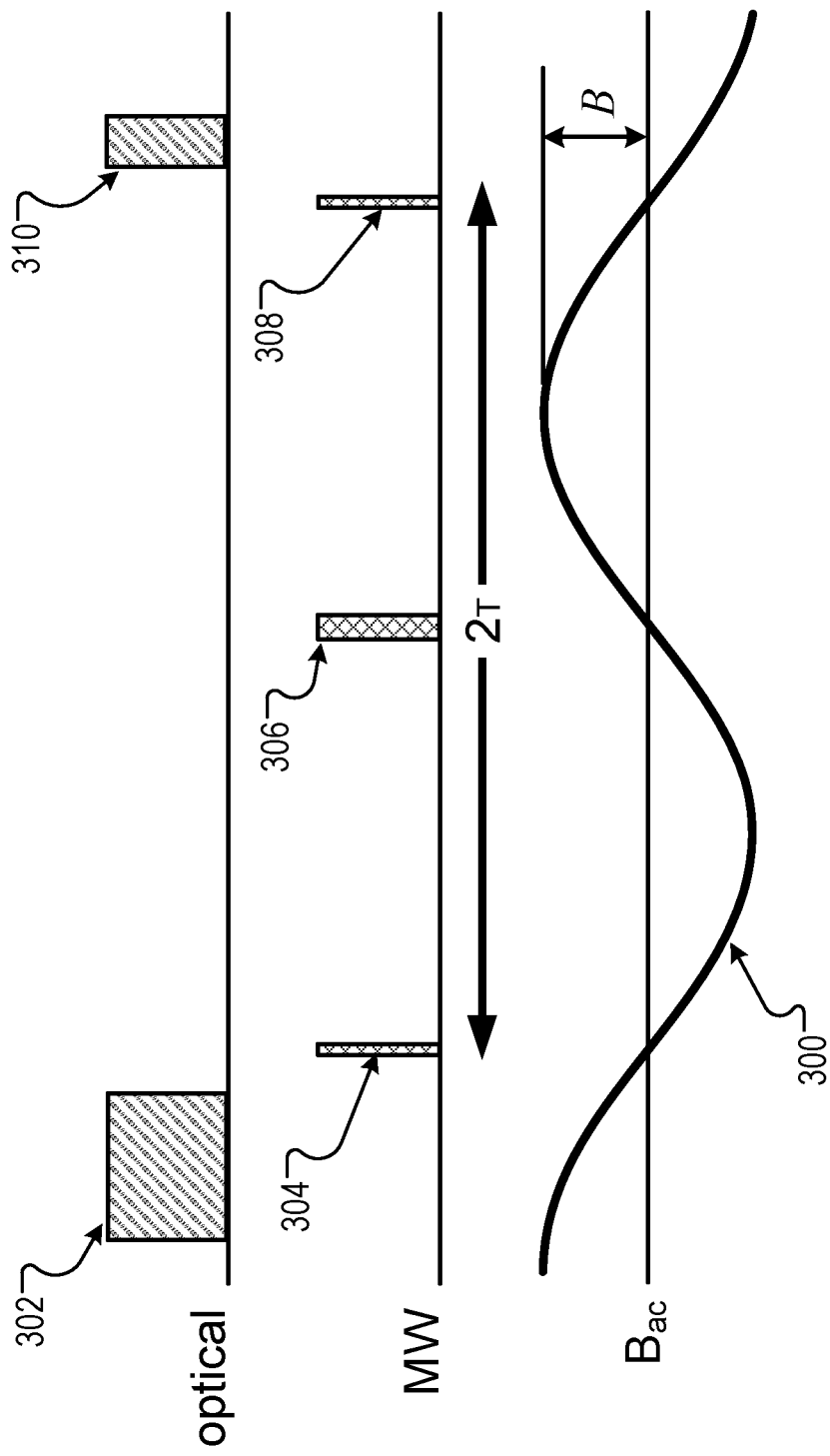
FIG. 3 is a schematic that illustrates an exemplary process for performing electron spin defect based magnetometry to detect an AC magnetic field.

Magnetic field sensitivity can further be improved if the magnetic field to be measured is periodic in time (e.g., an AC field). The improvement in sensitivity with a classical AC field is a result of a prolongation of the NV spin coherence that can be achieved through dynamical decoupling of the central spin from its environment. To avoid broadening of the ESR linewidth caused by the laser readout process and the driving microwave field, the spin manipulation, spin readout and phase accumulation (magnetic field measurement) may be separated in time. To do so, a series of microwave pulses are applied in sequence to the NV defect (or defects) that is in a prepared state $|0\rangle$. Here $|0\rangle$ and $|1\rangle$ denote the electron spin states $m_s=0$ and $m_s=1$. FIG. 3 is a schematic that illustrates an example of electron spin defect based magnetometry for an AC magnetic field, in which a microwave pulse sequence is be applied to an NV defect or ensemble of NV defects. The pulse sequence may also referred to as the "Hahn echo," though other dynamical decoupling pulse sequences may be used instead. In particular, a first light pulse 302 is applied to the NV defect, or ensemble of NV defects, to place them in a prepared state |0>. While the NV defect(s) are exposed to an alternating magnetic field 300, a first $\pi/2$ microwave pulse 304, is applied to the NV defect(s) to rotate the electron spin of the NV defect(s) from the prepared state |0> to a coherent superposition $|\psi>=1/\sqrt{2}*(|0>+e^{i\varphi}|1>)$ which evolves over a total free precession time $2\tau$, if the microwave drive Rabi frequency is larger than other terms in the Hamiltonian, such as NV hyperfine coupling, and the size of the magnetic field to be measured The phase $\varphi$ set to zero by definition, choosing the microwave drive field to be along the y axis (arbitrary). During the free precession time, the electron spin interacts with the external magnetic field. The |1> state acquires a phase with respect to the |0> state, corresponding to a precession of the spin in the plane perpendicular to the spin quantization axis in a Bloch sphere picture. Then, a first $\pi$ microwave pulse 306 is applied to "swap" the phase acquired by the |0> and |1> states. For slow components of the environmental magnetic noise, the dephasing acquired during the first half of the sequence is compensated and spin dephasing induced by random noise from the environment may be reduced. Additionally, frequency components much higher than the frequency $1/\tau$ average out to zero. Slow components may include, e.g., DC components and low frequency components on the order of several Hz, several tens of Hz, several hundreds of Hz, and 1-1000 kHz such as 10 Hz or less, 100 Hz or less, or 500 Hz or less, 1 kHz or less, 10 kHz or less, 100 kHz or less and 1 MHz or less. In some implementations, the pulse 306 is applied at the zero crossing of the classical AC magnetic field so that the spin phase accumulation due to the classical AC field can be enhanced. In some implementations, multiple $\pi$ microwave pulses 306 are applied periodically. After applying one or more $\pi$ microwave pulses 306, the phase $\varphi$ and thus the magnetic field is measured by applying a second $\pi/2$ pulse 308 that projects the NV electronic spin back onto the quantization axis. The total phase accumulation is thus converted into an electron population, which may be read out optically through the spin-dependent PL of the NV defect(s). That is, a second optical pulse 310 is applied to the NV defect, or ensemble of NV defects, resulting in a photoluminescence that is read out by an optical detector. To derive the magnetic field B(t) from the PL measurement, the function describing the evolution of the Sz operator under the pulse sequence is multiplied by the noise and signal fields, which is then integrated to get the phase accumulation and subsequently multiplied by contrast and total photoluminescence rate to get the photoluminescence signal (sine magnetometry). For cosine magnetometry, the filter function is convolved with the power spectral density of the noise and signal fields to get the phase variance, which is then multiplied by contrast and photoluminescence rate. Sensitivity compared to the continuous-wave driving technique may improve by a factor of at least $(T2/T2*)^{1/2}$, in which T2 is the coherence time of the NV under AC magnetometry and T2* is inversely proportional to the NV linewidth.

As explained above, an NV defect is just one example of a type of spin defect that may be used to perform electron spin defect based magnetometry. In other implementations, one or more spin defects may be formed in silicon carbide. SiC defects include defects due to other substitutional atoms, such as, e.g. phosphorus, in the SiC lattice. Similar techniques for detecting magnetic fields as described herein with NV defects may be employed with the SiC defects.

Figure 4:
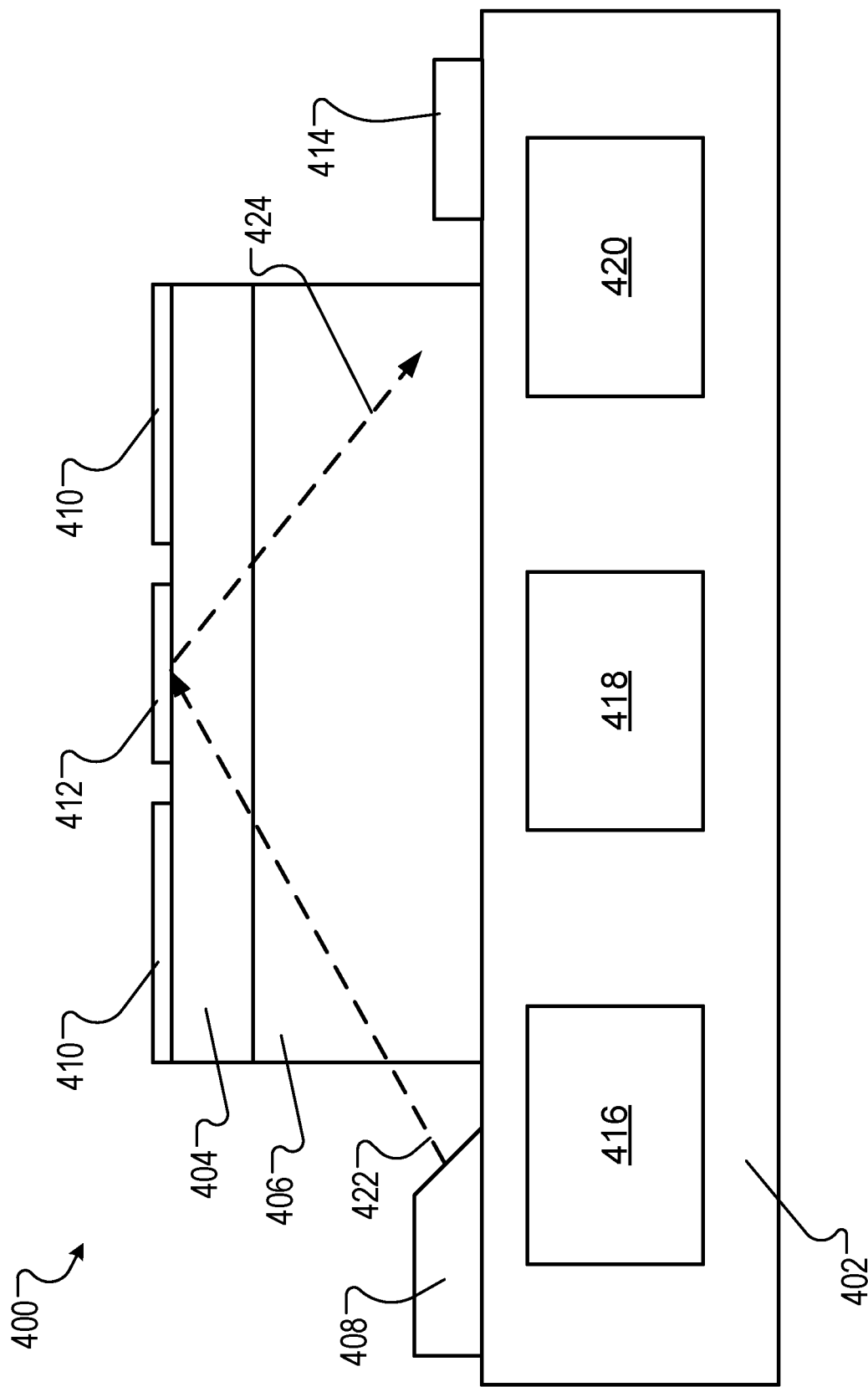
FIG. 4 is a schematic that illustrates an example of a device that may be used to perform electron spin defect based magnetometry.

FIG. 4 is a schematic that illustrates an example of a device 400 that may be used to perform electron spin defect based magnetometry, as described herein. Device 400 includes a substrate 402 and an electron spin defect layer 404 formed on the substrate 402. The electron spin defect layer 404 may include multiple lattice point defects, such as NV defects formed in diamond, as described herein. The defect layer 404 containing the NV defects may be formed, in some cases, from up to 99.999% carbon 12. In some implementations, carbon 13 may be used partially in place of carbon 12. The electron spin defect layer 404 is not limited to NV defects formed in diamond, which is typically electronic grade, and may include other lattice point defects in other materials, such as silicon carbide. The electron spin defect layer 404 may be a sub-layer of a larger layer 406 that is without the electron spin defects. For example, larger layer 406 may be a diamond layer without NV defects, whereas a top portion of the diamond layer corresponds to the defect layer 404.

The thickness of the defect layer 404 may vary. For example, in some implementations, the thickness of the defect layer 404 may be greater than about 2-3 microns, such as greater than 10 microns, greater than 50 microns, greater than 100 microns, greater than 250 microns, greater than 500 microns, or greater than 750 microns. The thickness of the defect layer 404 may be less than about 1 millimeter, such as less than 750 microns, less than 500 microns, less than 250 microns, or less than 100 microns. Other thicknesses may be used as well. Thickness of layer 404 is referenced here as being the distance from the interface between layer 404 and layer 406 and the opposite facing surface of layer 404. If the defect layer is a part of or formed on layer 406, then layer 406 may have its own separate thickness. For example, layer 406 may have a thickness between about 200 microns and about 5 millimeters. Thickness of layer 406 is referenced here as being the distance from the interface between layer 404 and layer 406 and the interface between layer 406 and substrate 402.

In some implementations, the layer 404 (or the layer 406) is secured to the substrate using an adhesive including, e.g., epoxies, elastomers, thermoplastics, emulsions, and/or thermosets, among other types of adhesives. In some implementations, electrical contacts are formed between the layer 404 (or the layer 406) and the substrate 402. For example, in some cases, the substrate may include a semiconductor material, such as silicon, in which one or more circuit elements (416, 418, 420) are fabricated. Electrical connections may be formed within the substrate 402 to provide an electrical connection between the circuit elements 416, 418, 420 and one or more components formed in or on layer 404 (or layer 406).

Device 400 further includes a microwave field transmitter 410 to provide a microwave field to the electron spin defects of the defect layer 404. In the present example shown in FIG. 4, microwave field transmitter 410 includes a thin film antenna formed on an upper surface of the defect layer 404. In some implementations, the microwave field transmitter 410 includes a patterned layer of metal on a surface of the defect layer 404, within layer 406 or at the interface between defect layer 404 and layer 406. The microwave field transmitter 410 may include a co-planar waveguide, a wire, a loop or a coil of electrically conductive material, such as metal. The microwave field transmitter 410 may be positioned adjacent to the area of the defect layer 404 to which the light from a spin defect excitation optical source is directed.

In some implementations, the device 404 includes a microwave field control circuit 416. The microwave field control circuit 416 may be formed in or on the substrate 402. For example, in some implementations, the control circuit 416 may be a circuit element formed within a silicon substrate. The control circuit 416 may be coupled, e.g., directly electrically connected, to the microwave field transmitter 410 to provide a microwave source signal to the microwave field transmitter 410 so that the microwave field transmitter 410 emits a microwave field toward the defect layer 404. The microwave source signal may optionally be a pulsed microwave source signal. In some implementations, a microwave frequency of the microwave source signal is between about 2 GHz and about 4 Ghz. In some implementations, the microwave field transmitter 410 emits signals at multiple frequencies spaced apart from one another to drive additional energy level splittings. For example, in some implementations, the microwave field transmitter 410 may be operated to emit microwave signals that address NV hyperfine transitions. In some implementations, the microwave control circuit 416 is configured to provide a control signal that generates a pulsed microwave signal at the transmitter 410. In some implementations, the microwave control circuit 416 is configured to provide a control signal that generates a continuous wave microwave signal at the transmitter 410.

In some implementations, the device 400 includes a photodetector 412 arranged to detect photoluminescence emitted from the electron spin defects of the defect layer 404. The photoluminescence may include one or more wavelengths of light, such as wavelengths of about 637 nm, corresponding to the emission wavelength of an NV defect. The photodetector 412 may be positioned on an upper surface of the defect layer 404 and in direct contact with the defect layer 404 as shown in FIG. 4. In some implementations, the photodetector 412 is positioned so that a detecting surface of the photodetector 412 faces an area of the defect layer 404 to which the light from an optical source is directed. The photodetector 412 may be secured to the defect layer 404 using an adhesive that is optically transparent to the wavelengths of light emitted by the NV defects. Alternatively, or in addition, the photodetector 412 may be formed beneath defect layer 404, such as at an interface between substrate 402 and layer 404 or within substrate 402. For example, in some implementations, the photodetector may be a silicon based photodetector formed within the substrate 402. In some implementations, an optical component is positioned between the photodetector 412 and the defect layer 404. For example, the optical component may include one or more of a lens, a beam-splitter, a diffraction grating, an optical filter, and/or a mirror. The optical filter may be configured to filter out wavelengths of light different than the wavelength of light emitted by the defects of the defect layer 404.

In some implementations, the device 404 includes a microprocessor 418, in which the microprocessor 418 is coupled to the photodetector 412 to receive a light measurement signal from the photodetector and in which the microprocessor is configured to analyze the light measurement signal to determine the characteristics of a magnetic field to which the device 404 is exposed. The microprocessor 418 may be formed in or on the substrate 402. For example, in some implementations, the microprocessor 418 may be a circuit element formed within a silicon substrate. The microprocessor 418 may be coupled, e.g., directly electrically connected, to the photodetector 412. In some implementations, the device 400 includes multiple photodetectors, such as a photodiode array. The photodetectors 412 may be located at multiple different positions around the defect layer 404 in order to maximize collection of light emitted by the defect layer 404. Though the microprocessor 418 is depicted as being formed in the substrate 402, the microprocessor may be located remotely from the magnetometer. For example, in some implementations, the magnetometer may include a transmitter/receiver to wirelessly receive control and analysis signals from the microprocessor 418 and to wirelessly transmit feedback and measurement data to the microprocessor.

In some implementations, the device 400 includes an optical source 408 configured to emit light. The light emitted by the optical source 408 may include a first wavelength that excites the one or more lattice point defects within the defect layer 404 from a ground state to an excited state. The first wavelength is different from a second wavelength that is emitted by the lattice point defects upon relaxation. The first wavelength may be, e.g., about 532 nm to excite NV defects in the defect layer 404. The optical source 408 may include, e.g., a light emitting diode, a laser, or a broadband source that includes filters configured to block transmission of wavelengths other than those used to excite the lattice point defects. The optical source 408 may be arranged to emit light 422 toward the defect layer 404. For example, the optical source 408 may be angled so that light 422 exiting the source 408 travels a path toward the defect layer 404. Alternatively, one or more optical elements may be positioned in front of the light emitted from the source 408 to redirect the light toward the defect layer 404. For example, the one or more optical components may include a lens, a mirror, a beam splitter, and/or a diffraction grating.

In some implementations, the device 404 includes an optical source circuit, i.e., a driver 420 for the optical source, in which the driver 420 is coupled to the optical source 408 to provide a control signal to drive the optical source. The driver 420 may be formed in or on the substrate 402. For example, in some implementations, the driver 420 may be a circuit element formed within a silicon substrate. The driver 420 may be coupled, e.g., directly electrically connected, to the optical source 408. In some implementations, the microprocessor 418 is coupled to one or both of the microwave field control circuit 416 and the driver 420 to control operation of the field control circuit 416 and/or the driver 420.

In some implementations, the device 400 includes a lock-in amplifier. For example, the microprocessor 418 and/or other circuit elements of the device 400 may include a lock-in amplifier coupled to an output of the photodetector 412 to match a timing and frequency of a reference signal provided by another circuit, e.g., the microprocessor 418, of the device 400.

In some implementations, at least one optical component is arranged between the optical source 408 and the defect layer, so that the at least one optical component is positioned to direct the light from the optical source 408 through the defect layer 404 and towards an interface of the defect layer 404 at an angle greater than a total internal reflection critical angle of an interface of the defect layer 404, such as shown in FIG. 4. In this way, the incident light 422 will be primarily reflected at the interface to provide reflected light 424 that can be recycled through the defect layer 404 to create additional excitation of lattice point defects. In some implementations, the device 400 includes optical fibers, such as tapered optical fibers, for optically coupling light into and out of the defect layer 404.

In some implementations, the device 400 includes a magnet 414. The magnet 414 may be arranged adjacent to the electron spin defect layer 404. The magnet 414 is provided to induce the Zeeman effect and lift the degeneracy of the ms=+/−1 spin sublevels. In some implementations, the magnet 414 is a permanent magnet. The magnet 414 may be positioned directly on the substrate 402m on layer 406, or on layer 404, among other locations. The magnet geometry may be chosen to minimize effects of inhomogeneous broadening between distinct defects in the defect layer 406.

In some implementations, the device 400 includes an optical resonator cavity including at least a portion of the electron spin defect layer and arranged to recycle the light through the electron spin defect layer. An exemplary variation of the magnetometer 400 is shown as device 500 in FIG. 5, with the exception that magnetometer 500 includes such an optical resonator. The optical resonator may be demarcated by the surfaces of the layer 406 and defect layer 404 that cause the incident light 422 to remain confined and/or to form a standing wave within a defined cavity space of the layers 404, 406. For instance, as explained herein, the light 422 may be directed at one or more surfaces, e.g., surface 502, of the layer 404 at angles that result in total internal reflection of the light 422. Alternatively, or in addition, reflective surfaces may be provided that redirect the light 422 to form part of a resonator optical path. For example, in some implementations, a surface 504 of the layer 404 and/or layer 406 through which light 422 is initially transmitted may be coated with a layer that is partially transmissive and partially reflective to the wavelength of light 422. Surface 508 and interface 510 may also include reflective surfaces. In some implementations, reflective surfaces, such as the surfaces and interfaces depicted in FIG. 5, include mirrors. The mirrors may be formed from deposited and polished metals such as silver or gold. In some implementations, the mirrors are formed from multiple layers of dielectric material with alternating refractive index, such as distributed Bragg reflectors. Alternatively, or in addition, the reflective surfaces may be formed by the material of layer 404 itself. For example, in some implementations, the defect layer 404 may include diamond structured to include multiple holes. The holes together with the diamond material may be designed and configured to cause Bragg reflection at predetermined locations of the defect layer 404 so that an optical resonator cavity is formed. In some implementations, the defect layer 404 may include a ring cavity resonator, such as, e.g., where the diamond is shaped like a disc or ring, and the light is introduced at a relatively small angle at the edge of the defect layer 404 such that undergoes TIR around all the edges of the layer 404 subsequent to entering the layer 404.

Figure 6:
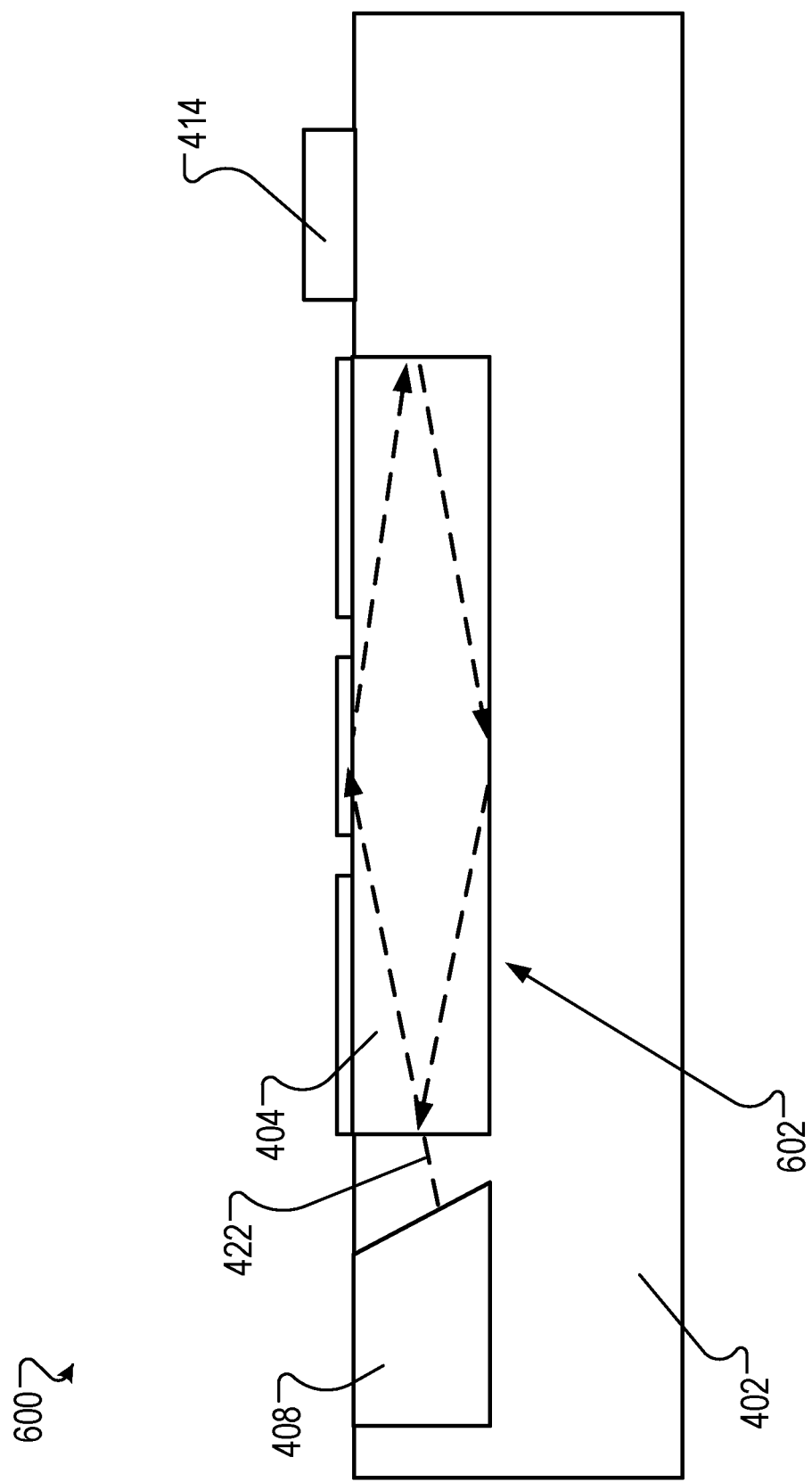
FIG. 6 is a schematic that illustrates an exemplary magnetometer.

In some implementations, the substrate 402 includes a recess, in which the defect layer 404 is seated within the recess. For example, FIG. 6 is a schematic that illustrates an alternative implementation 600 of the magnetometer 400 shown in FIG. 4. In FIG. 6, a section of the substrate 402 may be milled, etched, or removed in another way, to provide a recess 602 into which the layer 404 is positioned. Two or more walls of the recess 602 may be configured to be reflect light so that an optical resonator is formed, and the light is recycled within the defect layer 404. An additional advantage of this configuration is that certain features, such as the optical source 408 or the photodetector 412 may be formed within the substrate 402 as well, allowing for a more compact magnetometer configuration.

Figure 5:
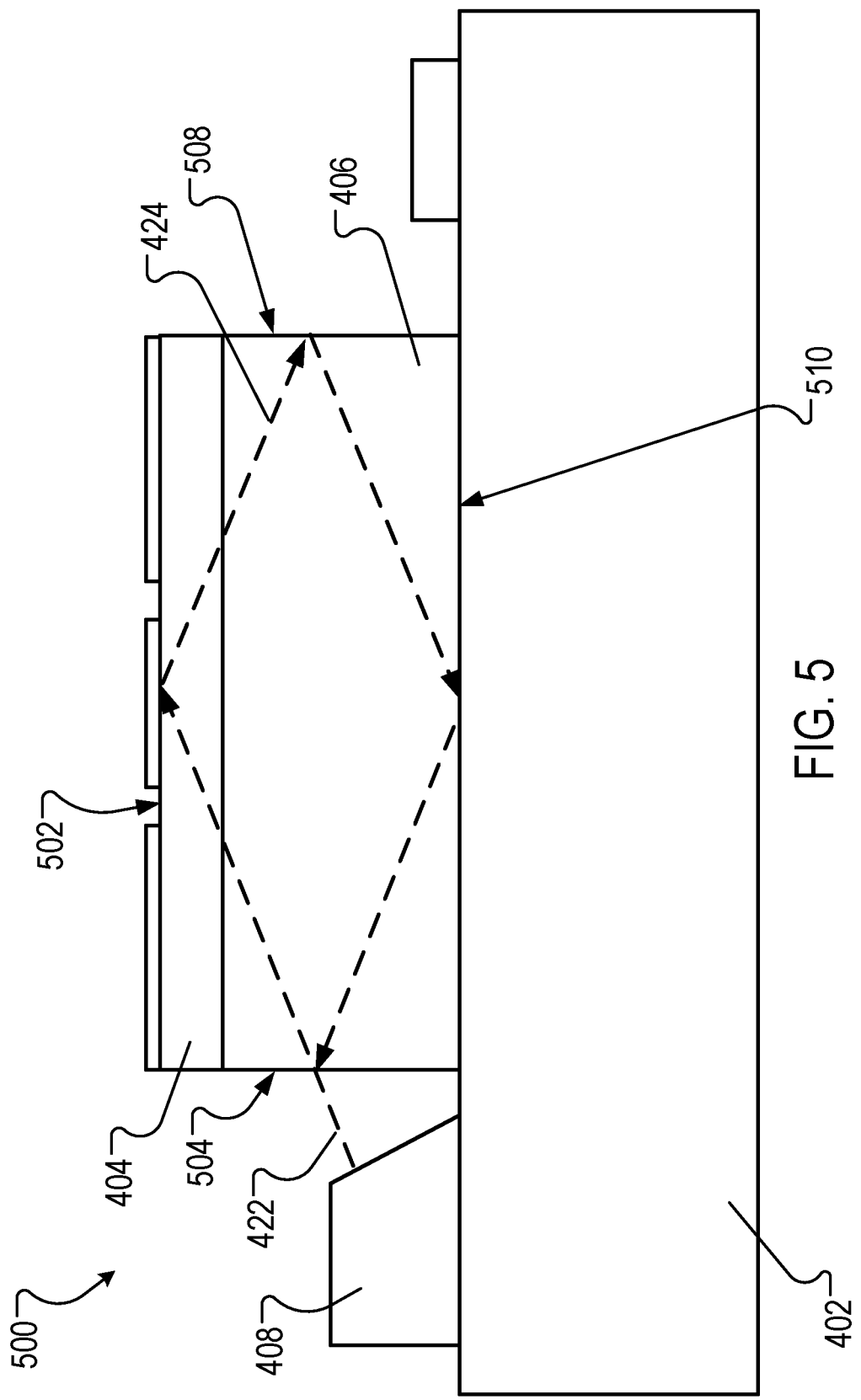
FIG. 5 is a schematic that illustrates an exemplary magnetometer.

In some implementations, the components described herein form the magnetometer, such as the exemplary devices shown in FIGS. 4-6, may be contained within an enclosure. The enclosure may be formed from a material that allows magnetic fields to pass freely to the magnetometer within the device, such as plastic. In some implementations, the enclosure may be covered partially or entirely by a thin thermally conducting layer of material such as, e.g., aerosol, for thermal isolation. In some implementations, the enclosure containing the magnetometer may be configured to attach to an article of clothing. In some implementations, the enclosure containing the magnetometer may be configured as part of a strap, belt, or other fastener that can be secured to a body. For example, the enclosure containing the magnetometer may be secured to a person's chest. Alternatively, or in addition, the magnetometer may be placed in others structure that are affixed to a body. In some implementations, the enclosure containing the magnetometer described herein may be configured to removably adhere to human skin using, e.g., a medically adhesive tape or other medical adhesive.

In some implementations, the magnetometer devices described herein including the substrate, the defect layer, the microwave field transmitter, the optical source, the optical resonator cavity, the photodetector and the magnet are arranged on a single chip.

In some implementations, the magnetic signal to be detected is a relatively low frequency (e.g., less than 1 kHz) signal or is a DC signal. In such cases, low frequency noise can crowd out the signal to be detected, i.e., reduce the signal to noise ratio. To reduce or eliminate the low frequency noise, the magnetometers as described herein may be rotated about an axis, such that the magnetic signal to be detected appears, to the magnetometer, to be a higher frequency signal. As explained herein, a pulsed-microwave detection method then may be used with high frequency signals to improve measurement sensitivity of the device.

Figure 7:
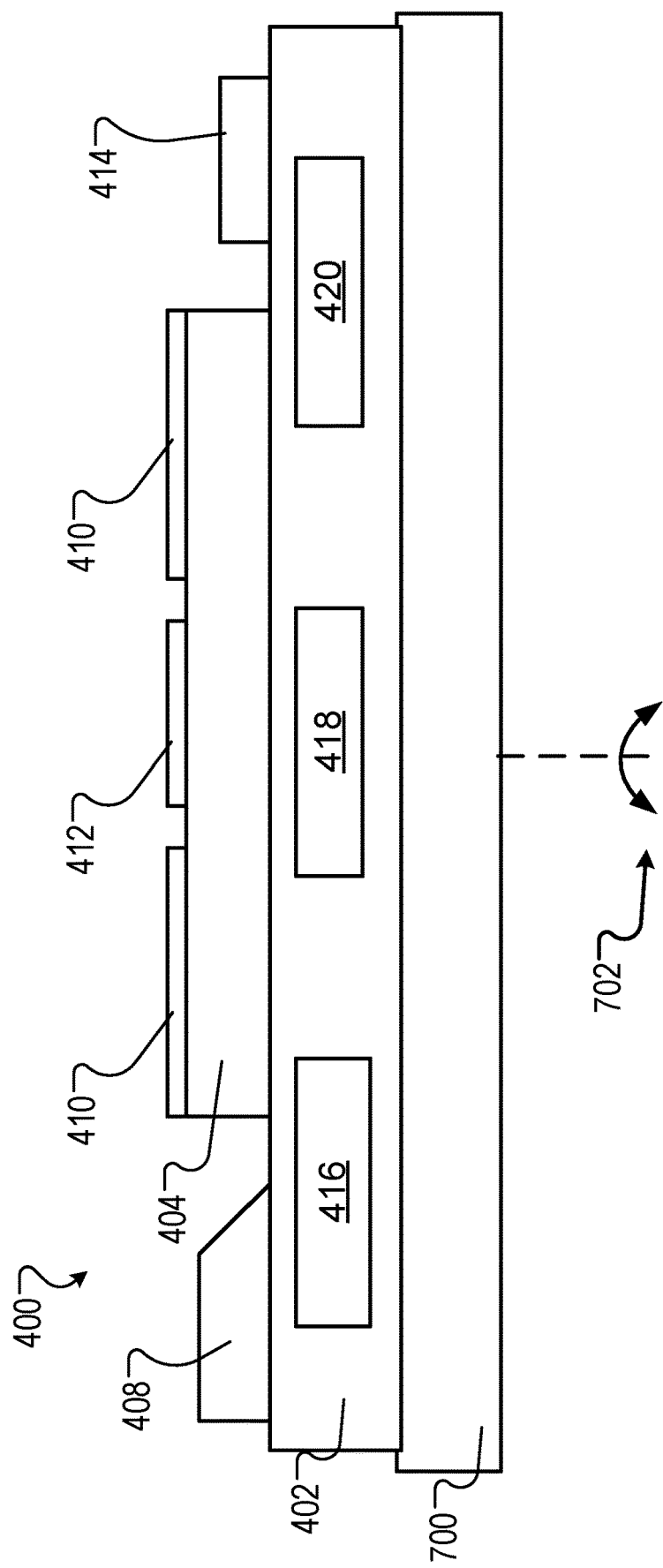
FIG. 7 is a schematic that illustrates an exemplary magnetometer.

To rotate the device, the magnetometer, such as the magnetometers described herein with respect to FIGS. 4-6, may be secured to a rotatable platform 700, as shown in FIG. 7, in which rotatable platform 700 has an axis of rotation 702. When the magnetometer 400 is secured to the rotatable platform 700, the platform 700 may spin the magnetometer 400 around the axis of rotation 702. Rotation of the device may include continuously spinning the magnetometer 400 around the rotation axis. Rotation of the device may alternatively include oscillating the magnetometer around the rotation axis at a rotation angle of less than 360 degrees. To use the pulsed-microwave detection method described herein, the frequency of rotation of the magnetometer is set to be greater than the frequency of the time-varying magnetic field to be detected. For example, the frequency of rotation may be 3 times greater, 10 times greater, 100 times greater, 1000 times greater, or 10,000 times greater than the frequency of the time-varying magnetic field to be detected.

In some implementations, the magnetometer including the defect layer, the optical source, the photodetector, the microwave field transmitter, and the magnet, is formed as an integrated circuit chip, i.e., a magnetometer chip. The magnetometer chip may be secured to the rotatable platform 700, such as a turntable. The turntable and magnetometer chip may be housed within an enclosure as described herein. To improve detection sensitivity, the magnetic vector field of the magnetic signal to be detected should be oriented in the plane of the intrinsic quantization axis of the defect within the defect layer so that projection of the magnetic field along the quantization axis changes as much as possible during rotation of the device. Taking as an example the NV defect, the quantization axis corresponds to the axis joining the nitrogen and the vacancy. Thus, there are four orientations of NVs in an NV defect layer of diamond, and therefore four different options for aligning the magnetic vector field with a quantization axis. Alternatively, the magnetic field vector will have projections along all four NV orientation axis, which could be addressed simultaneously to recover vector information about the magnetic field. In an example implementation, the device may be oriented so that the axis of rotation is aligned to be substantially perpendicular to the magnetic field vector of the signal to be detected and therefore the quantization axis of the interrogated defects. In the case the alignment is not precise or there is some background movement (e.g., in the case the device is placed on or near a person and the person's movement causes the alignment of the quantization axis and the magnetic field to constantly change), such relatively low frequency movement may be filtered out using the pulsed-microwave detection method described herein and in post-processing.

In some implementations, the techniques disclosed herein may allow the magnetometer, without rotation, to obtain sensitivities less than 100 pT/√Hz, such as less than 15 pT/√Hz. In some implementations, the techniques disclosed herein may allow the magnetometer, with rotation, to obtain sensitivities less than 50 pT/√Hz, such as less than 10 pT/√Hz or 1 pT/√Hz.

The electron spin defect based magnetometry techniques and devices described herein are viable for compact, room temperature magnetometry, and are robust to large magnetic field variations. In some implementations, the magnetometer can be used in applications such as magnetocardiography to detect magnetic fields from the heart. In particular, compact, robust spin defect based magnetometers may be used to detect magnetic fields emanating from the heart for continuous, long-term monitoring and early detection of various cardiac conditions.

Cardiovascular disease is the number one cause of death worldwide. Electric and magnetic fields generated by the heart contain information about the onset of a dangerous condition such as a heart attack or arrhythmia. However, technologies for monitoring this vital organ may be bulky, noisy, and in non-clinical settings can only be used for up to a few days at a time, making the continuous acquisition of data over at best problematic. Moreover, current analyses must be performed by a medical professional after the data is taken, severely limiting the amount of data that can be analyzed and further increasing the cost (and decreasing the scope and accessibility) of these vital services.

The sensors required to detect the small magnetic fields tend to require operation in a shielded room (such as optically pumped magnetometers), or at cold temperatures (such as SQUIDS), making continuous acquisition and monitoring difficult. The magnetometers disclosed herein may be used, in certain implementations, as quantum sensors to measure magnetic fields from the heart and may be operated outside of a shielded room, at room temperature and offer a large dynamic range of up to 100 mT. Moreover, the device may be constructed so it is compact and can be worn comfortably and close to the body.

Figure 8:
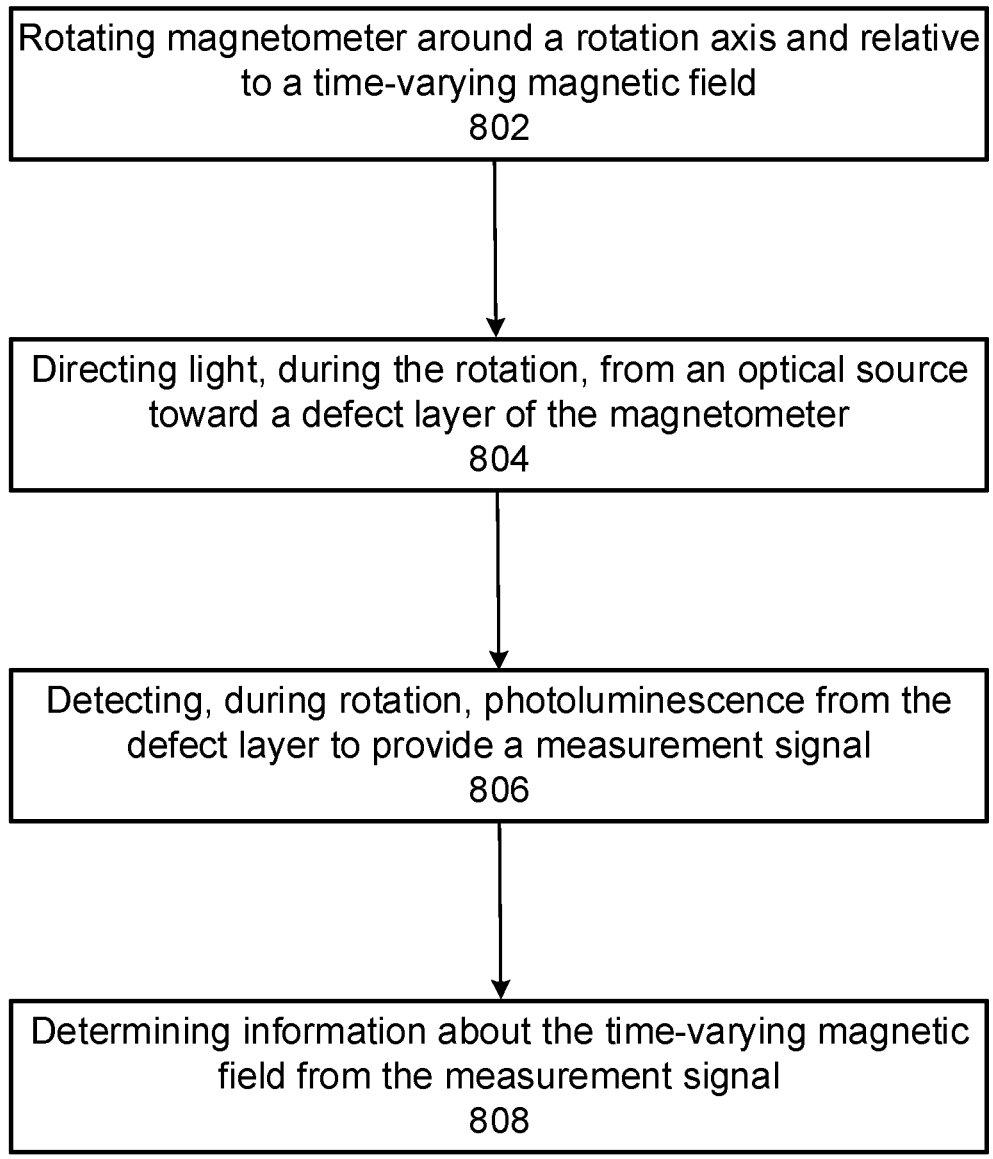
FIG. 8 is a schematic that illustrates an exemplary process for detecting a magnetic field using a magnetometer.

FIG. 8 is a schematic that illustrates an exemplary process 800 for detecting a magnetic field using a magnetometer, such as the magnetometers described herein. As shown in FIG. 8, the process 800 may include rotating (802) the magnetometer around a rotation axis and relative to a first time-varying magnetic field of a first frequency so that the magnetometer experiences a second time-varying magnetic field of a second frequency that is greater than the first frequency. In a second step, light is directed (804), during the rotation of the magnetometer, from an optical source toward a defect layer of the magnetometer, in which the defect layer includes multiple lattice point defects. The light may include a first wavelength that excites the lattice point defects from a ground state to an excited state. Process 800 further may include detecting (806), during the rotation of the magnetometer, a photoluminescence from the defect layer using a photodetector to provide a measurement signal, in which the photoluminescence includes a second wavelength that is different from the first wavelength. The process 800 further may include determining (808), from the measurement signal, information about the first time-varying magnetic field.

Rotating the magnetometer may include continuously spinning the magnetometer around a rotation axis or oscillating the magnetometer around the rotation axis at a rotation angle of less than 360 degrees. Directing the light from the optical source toward the electron spin defect layer may include directing the light from the optical source through the electron spin defect layer so that the light impinges on an interface of the electron spin defect layer at an angle greater than a total internal reflection critical angle of the interface. Directing the light from the optical source toward the electron spin defect layer may include redirecting, using an optical resonator cavity, totally internally reflected light from the interface of the electron spin defect layer back to the interface of the electron spin defect layer.

In some implementations, the process 800 further includes applying a microwave signal to the electron spin defect layer. Applying the microwave signal optionally includes applying a series of microwave pulses, in which the series of microwave pulses is optionally a dynamical decoupling pulse sequence, such as a Hahn echo sequence. The series of pulses may include a first pi/2 pulse, one or more pi pulses subsequent to the first pi/2 pulse, and a second pi/2 pulse subsequent to the first pi pulse. The one or more pi pulses may be applied at a same time as a zero-crossing of the second time-varying magnetic field. A frequency of rotation of the magnetometer may be greater than a frequency of the first time-varying magnetic field. The frequency of the first time-varying magnetic field may be less than 300 Hz.

In some implementations, the process 800 includes: prior to rotating the magnetometer, sweeping a frequency of the microwave source signal over a predetermined range; and identifying a reduction in photoluminescence from the photodetector at a first microwave frequency within the predetermined range to locate an electron spin resonance frequency.

In some implementations, determining information about the first time-varying magnetic field includes: extracting a quantum phase accumulation from the measurement signal of the photodetector; and determining a magnitude of the first time-varying magnetic field, a phase of the first time-varying magnetic field or both the magnitude and the phase of first time-varying magnetic field from the quantum phase accumulation.

The first time-varying magnetic field may be emitted from a biological organism, such as a human. In some implementations, the first time-varying magnetic field is emitted from a heart, such as a human heart. In some implementations, the process 800 includes attaching an enclosure comprising the magnetometer to an article of clothing. In some implementations, the biological organism is a mammal, and the process 800 includes adhering an enclosure comprising the magnetometer to skin of the mammal.

Embodiments and functional operations described in this specification, such as the operations and analysis performed by the microprocessor, the microwave control circuit, and the optical source driver, may be implemented in digital electronic circuitry, or in computer software, firmware, or hardware, including the structures disclosed in this specification and their structural equivalents, or in combinations of one or more of them. Embodiments may be implemented as one or more computer program products, i.e., one or more modules of computer program instructions encoded on a computer readable medium for execution by, or to control the operation of, data processing apparatus. The computer readable medium may be a machine-readable storage device, a machine-readable storage substrate, a memory device, a composition of matter effecting a machine-readable propagated signal, or a combination of one or more of them.

The term "data processing apparatus" encompasses all apparatus, devices, and machines for processing data, including by way of example a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) may be written in any form of programming language, including compiled or interpreted languages, and it may be deployed in any form, including as a stand-alone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform functions by operating on input data and generating output. The processes and logic flows may also be performed by, and apparatus may also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both.

While this specification contains many specifics, these should not be construed as limitations on the scope of the disclosure or of what may be claimed, but rather as descriptions of features specific to particular embodiments. Certain features that are described in this specification in the context of separate embodiments may also be implemented in combination in a single embodiment. Conversely, various features that are described in the context of a single embodiment may also be implemented in multiple embodiments separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products A number of embodiments have been described. Nevertheless, it will be understood that various modifications may be made without departing from the spirit and scope of the invention. Accordingly, other embodiments are within the scope of the following claims.

What is claimed is:

1. A magnetometer comprising:
   a substrate;
   an electron spin defect layer on the substrate, wherein the electron spin defect layer comprises a plurality of lattice point defects;
   a microwave field transmitter;
   an optical source configured to emit light comprising a first wavelength that excites the plurality of lattice point defects from a ground state to an excited state;
   an optical resonator cavity defined by at least three surfaces, on at least three sides of the optical resonator cavity, that are arranged to reflect the light within the optical resonator cavity to recycle the light through the electron spin defect layer,
   wherein the light from the optical source is transmitted into the optical resonator cavity through a first surface of the at least three surfaces, and
   wherein at least a portion of the electron spin defect layer constitutes one or more of the at least three surfaces of the optical resonator cavity;
   a photodetector arranged to detect photoluminescence comprising a second wavelength emitted from the electron spin defect layer, wherein the first wavelength is different from the second wavelength; and
   a magnet arranged adjacent to the electron spin defect layer.

2. The magnetometer of claim 1, wherein the substrate comprises a microwave field control circuit coupled to the microwave field transmitter, wherein the microwave field control circuit is configured to provide the microwave field transmitter with a microwave source signal,
   wherein the microwave field control circuit is configured to output the microwave source signal as a pulsed microwave source signal, and wherein the microwave field control circuit is configured to output the microwave source signal at a frequency between 50 MHz and 4 GHz.

3. The magnetometer of claim 1, wherein the substrate comprises an optical source control circuit coupled to the optical source and configured to provide the optical source with an optical control signal.

4. The magnetometer of claim 1, wherein the substrate comprises a microprocessor, wherein the microprocessor is coupled to the photodetector and configured to receive a light measurement signal from the photodetector, and
wherein the microprocessor is configured to analyze the light measurement signal to determine characteristics of a time-dependent magnetic field to which the magnetometer is exposed.

5. The magnetometer of claim 1, wherein the plurality of lattice point defects comprises a plurality of nitrogen-vacancy (NV) defects, wherein the electron spin defect layer comprises a diamond layer comprising carbon 12 and/or carbon 13.

6. The magnetometer of claim 1, wherein the plurality of lattice point defects comprises a plurality of silicon-carbide (SiC) defects.

7. The magnetometer of claim 1, wherein the electron spin defect layer has a thickness of between 1 micron and 1 mm.

8. The magnetometer of claim 1, wherein the microwave field transmitter comprises a patterned layer of metal on a surface of the electron spin defect layer or at an interface of the electron spin defect layer and another layer of material.

9. The magnetometer of claim 1, wherein the optical source comprises a light emitting diode or a laser.

10. The magnetometer of claim 9, wherein the optical source is arranged to emit light towards the electron spin defect layer such that the light travels through the electron spin defect layer and impinges on an interface of the electron spin defect layer at an angle greater than a total internal reflection critical angle of the interface.

11. The magnetometer of claim 1, wherein the optical resonator cavity comprises a plurality of mirrors.

12. The magnetometer of claim 11, wherein at least one mirror of the plurality of mirrors is partially transmissive to a wavelength of the light from the optical source and is arranged between the optical source and the electron spin defect layer.

13. The magnetometer of claim 1, wherein the substrate comprises a recess, wherein the electron spin defect layer is seated within the recess, wherein the recess comprises at least one reflective sidewall facing the electron spin defect layer to reflect the light from the optical source towards the electron spin defect layer or to redirect the light from the optical source that has been reflected from the electron spin defect layer.

14. The magnetometer of claim 1, comprising at least one optical filter between the electron spin defect layer and the photodetector, wherein the at least one optical filter is configured to filter out wavelengths of light different than the second wavelength.

15. The magnetometer of claim 1, comprising an enclosure, wherein the substrate, the electron spin defect layer, the microwave field transmitter, the optical source, the optical resonator cavity, the photodetector and the magnet are contained in the enclosure.

16. The magnetometer of claim 1, comprising a rotatable platform, wherein the substrate, the electron spin defect layer, the microwave field transmitter, the optical source, the optical resonator cavity, the photodetector and the magnet are arranged on a single chip, and wherein the single chip is secured to the rotatable platform having an axis of rotation, and the rotatable platform is configured to spin the single chip around the axis of rotation.

17. The magnetometer of claim 1, wherein at least one surface of the at least three surfaces comprises an interface between the electron spin defect layer and the substrate.

18. The magnetometer of claim 1, wherein the optical resonator cavity is defined by at least four surfaces, on at least four sides of the optical resonator cavity, that are arranged to reflect the light within the optical resonator cavity to recycle the light through the electron spin defect layer.

19. The magnetometer of claim 1, wherein the at least three surfaces and the optical source are arranged such that the light reflects sequentially off each of the at least three surfaces.

20. The magnetometer of claim 1, wherein the photodetector is disposed on a surface of the at least three surfaces of the optical resonator cavity.

21. The magnetometer of claim 1, wherein the microwave field transmitter is disposed on a surface of the at least three surfaces of the optical resonator cavity.

* * * * *

UNITED STATES PATENT AND TRADEMARK OFFICE
CERTIFICATE OF CORRECTION

| | |
|---|---|
| PATENT NO. | : 11,733,321 B2 |
| APPLICATION NO. | : 17/062028 |
| DATED | : August 22, 2023 |
| INVENTOR(S) | : Rosenfeld |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 108 days.

Signed and Sealed this
Twelfth Day of November, 2024

*Katherine Kelly Vidal*

Katherine Kelly Vidal
*Director of the United States Patent and Trademark Office*